US009744072B1

(12) United States Patent
Qiang

(10) Patent No.: US 9,744,072 B1
(45) Date of Patent: Aug. 29, 2017

(54) DEVICES AND METHODS FOR MANAGING INSULIN RESISTANCE

(71) Applicant: Gludone Inc., San Jose, CA (US)

(72) Inventor: Li Qiang, Fort Lee, NJ (US)

(73) Assignee: Gludone Inc., San Jose, CA (US)

( * ) Notice: Subject to any disclaimer, the term of this patent is extended or adjusted under 35 U.S.C. 154(b) by 0 days.

(21) Appl. No.: 15/465,259

(22) Filed: Mar. 21, 2017

Related U.S. Application Data

(60) Provisional application No. 62/362,629, filed on Jul. 15, 2016.

(51) Int. Cl.
*A61H 39/00* (2006.01)
*A61F 7/00* (2006.01)

(52) U.S. Cl.
CPC ......... *A61F 7/0085* (2013.01); *A61H 39/002* (2013.01); *A61F 2007/0011* (2013.01); *A61F 2007/0056* (2013.01); *A61F 2007/0086* (2013.01); *A61H 2205/04* (2013.01)

(58) Field of Classification Search
CPC .............................. A61H 39/002; A61H 39/06
See application file for complete search history.

(56) References Cited

U.S. PATENT DOCUMENTS

| | | | | |
|---|---|---|---|---|
| 9,238,133 | B2 * | 1/2016 | Boyden | A61N 1/0534 |
| 2007/0203431 | A1 * | 8/2007 | Leta | A61F 7/0053 |
| | | | | 601/2 |
| 2012/0290023 | A1 * | 11/2012 | Boyden | A61N 5/025 |
| | | | | 607/3 |
| 2012/0290051 | A1 * | 11/2012 | Boyden | A61F 7/12 |
| | | | | 607/113 |
| 2014/0018767 | A1 * | 1/2014 | Harris | A61M 5/14276 |
| | | | | 604/500 |
| 2014/0088487 | A1 * | 3/2014 | Harris | A61M 5/14276 |
| | | | | 604/20 |
| 2015/0119849 | A1 * | 4/2015 | Aronhalt | A61F 7/10 |
| | | | | 604/506 |
| 2015/0328460 | A1 * | 11/2015 | Greiner | A61N 1/36071 |
| | | | | 607/46 |

(Continued)

OTHER PUBLICATIONS

WHO. Obesity: preventing and managing the global epidemic. Report of a WHO consultation. *World Health Organization technical report series.* 2000;894:i-xii, 1-253.

(Continued)

*Primary Examiner* — Kaitlyn Smith
(74) *Attorney, Agent, or Firm* — Lihua Zheng; Liu Zheng Chen & Hoffman LLP

(57) ABSTRACT

Disclosed are devices and methods for mitigating insulin resistance in a human subject by contacting one or more regions of the neck, the supraclavicular, and the interscapular regions of the human subject with a part of a cooling device, wherein the part of the cooling device has a temperature at about 15 or less Celsius degrees; cooling the one or more regions of the neck, the supraclavicular, and the interscapular regions of the human subject for a cooling period of at least 15 minutes; and performing previous two steps daily for about 14 or more days. The devices and methods may also be used to preventing, delaying or treating type 2 diabetes in a human subject or activating brown fat without incurring a sympathetic nerve-mediated cold feeling in a human subject.

26 Claims, 7 Drawing Sheets

(56) References Cited

U.S. PATENT DOCUMENTS

| | | | | | |
|---|---|---|---|---|---|
| 2015/0374538 | A1* | 12/2015 | Rogers | .................... | A61K 31/00 607/105 |
| 2016/0058610 | A1* | 3/2016 | Ryotokuji | .............. | A61H 39/04 606/189 |
| 2016/0143771 | A1* | 5/2016 | Swyer | .................... | A61F 7/0085 607/104 |
| 2016/0242954 | A1* | 8/2016 | Ryotokuji | ............... | A61F 7/007 |

OTHER PUBLICATIONS

Stevens GA, Singh GM, Lu Y, Danaei G, Lin JK, Finucane MM, et al. National, regional, and global trends in adult overweight and obesity prevalences. *Population health metrics*. 2012;10(1):22.

CDC. National Diabetes Statistics Report: Estimates of Diabetes and Its Burden in the United States, 2014. *US Department of Health and Human Services*. 2014.

Ahmadian M, Suh JM, Hah N, Liddle C, Atkins AR, Downes M, et al. PPARgamma signaling and metabolism: the good, the bad and the future. *Nat Med*. 2013;19(5):557-66.

Stein SA, Lamos EM, and Davis SN. A review of the efficacy and safety of oral antidiabetic drugs. *Expert opinion on drug safety*. 2013;12(2):153-75.

Lee P, Smith S, Linderman J, Courville AB, Brychta RJ, Dieckmann W. et al.Temperature-acclimated brown adipose tissue modulates insulin sensitivity in humans. *Diabetes*. 2014;63(11):3686-98.

Hanssen MJ, Hoeks J, Brans B, Van Der Lans AA, Schaart G, Van Den Driessche JJ, et al. Short-term cold acclimation improves insulin sensitivity in patients with type 2 diabetes mellitus. *Nat Med*. 2015;21(8):863-5.

Cannon B, and Nedergaard J. Brown adipose tissue: function and physiological significance. *Physiological reviews*. 2004;84(1):277-359.

Cannon B, Houstek J, and Nedergaard J. Brown adipose tissue. More than an effector of thermogenesis? *Ann N Y Acad Sci*. 1998;856:171-87.

Cannon B, Shabalina IG, Kramarova TV, Petrovic N, and Nedergaard J. Uncoupling proteins: a role in protection against reactive oxygen species—or not? *Biochim Biophys Acta*. 2006;1757(5-6):449-58.

Kajimura S, Seale P, and Spiegelman BM. Transcriptional control of brown fat development. *Cell Metab*. 2010;11(4):257-62.

Rosen ED, and Spiegelman BM. What we talk about when we talk about fat. *Cell*. 2014;156(1-2):20-44.

Harms M, and Seale P. Brown and beige fat: development, function and therapeutic potential. *Nat Med*. 2013 ;19(10): 1252-63.

Wu J, Cohen P, and Spiegelman BM. Adaptive thermogenesis in adipocytes: is beige the new brown? *Genes Dev*. 2013;27(3):234-50.

Cypess AM, Haft CR, Laughlin MR, and Hu HH. Brown fat in humans: consensus points and experimental guidelines. *Cell Metab*. 2014;20(3):408-15.

Buemann B, Toubro S, and Astrup A. Effects of the two beta3-agonists, ZD7114 and ZD2079 on 24 hour energy expenditure and respiratory quotient in obese subjects. *Int J Obes Relat Metab Disord*. 2000;24(12):1553-60.

Arch Jr. beta(3)-Adrenoceptor agonists: potential, pitfalls and progress. *European journal of pharmacology*. 2002;440(2-3):99-107.

Mullur R, Liu YY, and Brent GA. Thyroid hormone regulation of metabolism. *Physiological reviews*. 2014;94(2):355-82.

Chen W, Yang Q, and Roeder RG. Dynamic interactions and cooperative functions of PGC-1alpha and MED1 in TRalpha-mediated activation of the brown-fat-specific UCP-1 gene. *Molecular cell*. 2009;35(6):755-68.

Wei W, Dutchak PA, Wang X, Ding X, Wang X, Bookout AL, et al. Fibroblast growth factor 21 promotes bone loss by potentiating the effects of peroxisome proliferator-activated receptor gamma. *Proc Natl Acad Sci U S A*. 2012;109(8):3143-8.

Sun K, Kusminski CM, Luby-Phelps K, Spurgin SB, AN YA, Wang QA, et al. Brown adipose tissue derived VEGF-A modulates cold tolerance and energy expenditure. *Molecular metabolism*. 2014;3(4):474-83.

Goel HL, and Mercurio AM. VEGF targets the tumour cell. *Nature reviews Cancer*. 2013;13(12):871-82.

YE L, WU J, Cohen P, Kazak L, Khandekar MJ, Jedrychowski MP, et al. Fat cells directly sense temperature to activate thermogenesis. *Proc Natl Acad Sci U S A*. 2013;110(30):12480-5.

* cited by examiner

DEVICES AND METHODS FOR MANAGING INSULIN RESISTANCE

CROSS-REFERENCE TO RELATED APPLICATIONS

This application claims the benefit of priority of earlier-filed U.S. Provisional Patent Application Nos. 62/362,629, filed on Jul. 15, 2016, the disclosure of which application is incorporated herein by reference.

FIELD OF INVENTION

The invention relates generally to the field of medical devices, specifically devices for managing diabetes, more specifically for managing insulin resistance, and methods for managing physiological conditions, specially diabetes, more specifically insulin resistance.

BACKGROUND

Easy access to calorie and sedentary life styles have led to the pandemics of Type 2 diabetes to affect over one billion adults and a lot more in the prediabetic insulin resistance stage (1, 2). Currently, in the United States alone, there are over 29 million people diagnosed with type 2 diabetes, which cost $245 billion annually (3).

Type 2 diabetes is characterized by insulin resistance, which may be combined with relatively reduced insulin secretion. Type 2 diabetes is a chronic disease, for which there is no known cure except in very specific situations. Type 2 Diabetes management concentrates on keeping blood sugar levels as close to normal, without causing low blood sugar. The current methods of type 2 diabetes management include a healthy diet, exercise, weight loss, and use of appropriate medications. Those medications include, among others, Metformin, as well as possibly insulin.

Current medications for treating Type 2 diabetes can cause deleterious effects to various extents. For example, thiazolidinedione (TZDs, Actos, Avandia), an insulin sensitizer for treating type 2 diabetes, can cause body weight gain, heart failure, fracture and certain types of cancer (4, 5). Therefore, there is an urgent need to develop more effective and safer treatments for Type 2 diabetes.

In a recent study, a human being who stayed in climate-controlled rooms at 19° C. for one month, or 14-15° C. for 10 days, had significantly increased insulin sensitivity (6, 7). However, these current approaches are not practically operational for clinical utilizations, nor are preferred by patients because of the uncomfortableness of cold.

Acupuncture is considered to be an effective therapy for regulating pain and managing many other functions of the body, for example chronic muscle spasm and neurological dysfunctions. More recently, electroacupuncture (EA) was developed and shown to significantly enhance traditional acupuncture treatments. EA are similar to traditional acupuncture except that the needles are attached to a device that sends electrical currents or pulses into the body.

BRIEF SUMMARY OF THE INVENTION

In one aspect, the disclosed invention is directed to a method for mitigating insulin resistance in a human subject by contacting one or more regions of the neck, the supraclavicular, and the interscapular regions of the human subject with a part of a cooling device, wherein the part of the cooling device has a temperature at about 15 or less Celsius degrees; cooling the one or more regions of the neck, the supraclavicular, and the interscapular regions of the human subject for a cooling period of at least 15 minutes; and performing the above two steps for one or more times daily for about 14 or more days.

In some embodiments of the method for mitigating insulin resistance in a human subject, the part of the cooling device has a temperature ranging from about 4 to about 15 Celsius degrees. In other embodiments, the part of the cooling device has a temperature ranging from about −15 to about 4 Celsius degrees. In some embodiments, the cooling period ranges from about 15 to about 30 minutes. In other embodiments, the cooling period ranges from about 30 minutes to about 2 hours. In still other embodiments, the cooling period ranges from about 2 to about 4 hours. In some embodiments, the cooling device has a temperature controller that can be used to adjust the temperature of the part of the cooling device that contacts the human subject.

In some embodiments, the method for mitigating insulin resistance in a human subject further comprises the step of applying electroacupuncture to one or more regions selected from the group consisting of the neck, the supraclavicular and the interscapular regions in the second step. In some instances, the electroacupuncture is applied simultaneously during the cooling period. In other instances, the electroacupuncture is applied prior to the cooling period. In still other instances, the electroacupuncture is applied in a period that overlaps the cooling period.

In some embodiments of the method for mitigating insulin resistance in a human subject, the cooling treatment is performed once daily for 14 or more days. In other embodiments, the cooling treatment is performed twice daily for 14 or more days. In still other embodiments, the cooling treatment is performed thrice daily for 14 or more days.

In another aspect, the disclosed invention is directed to a method for preventing, delaying or treating type 2 diabetes in a human subject by contacting one or more regions of the neck, the supraclavicular, and the interscapular regions of the human subject with a part of a cooling device, wherein the part of the cooling device has a temperature at about 15 or less Celsius degrees; cooling the one or more regions of the neck, the supraclavicular, and the interscapular regions of the human subject for a cooling period of at least 15 minutes; and performing the above two steps one or more times daily for about 14 or more days.

In some embodiments of the method for preventing, delaying or treating type 2 diabetes in a human subject, the part of the cooling device has a temperature ranging from about 4 to about 15 Celsius degrees. In other embodiments, the part of the cooling device has a temperature ranging from about −15 to about 4 Celsius degrees. In some embodiments, the cooling period ranges from about 15 to about 30 minutes. In other embodiments, the cooling period ranges from about 30 minutes to about 2 hours. In still other embodiments, the cooling period ranges from about 2 to about 4 hours. In some embodiments, the cooling device has a temperature controller that can be used to adjust the temperature of the part of the cooling device that contacts the human subject.

In some embodiments, the method for preventing, delaying or treating type 2 diabetes in a human subject further comprises the step of applying electroacupuncture to one or more regions selected from the group consisting of the neck, the supraclavicular and the interscapular regions in the second step. In some instances, the electroacupuncture is applied simultaneously during the cooling period. In other instances, the electroacupuncture is applied prior to the cooling period. In still other instances, the electroacupuncture is applied in a period that overlaps the cooling period.

In some embodiments of the method for preventing, delaying or treating type 2 diabetes in a human subject, the cooling treatment is performed once daily for 14 or more days. In other embodiments, the cooling treatment is performed twice daily for 14 or more days. In still other embodiments, the cooling treatment is performed thrice daily for 14 or more days.

In yet another aspect, the disclosed invention is directed to a cooling device that comprises a body-contacting vest that directly contacts one or more regions of the neck, the supraclavicular and the interscapular regions; a tube that is filled with cooling media, said tube partially contacts the body-contacting vest; and a refrigeration part that cools the cooling media in the tube, said cooling media in turn cools the body-contacting vest to a specified temperature of 15 Celsius degree or below.

In some embodiments of the cooling device, the body-contacting vest is made of fabric. In other embodiments, the body-contacting vest is made of carbon fibers. In still other embodiments, the body-contacting vest is made of metal.

In some embodiments of the cooling device, the refrigeration part is a cyclic refrigeration. In other embodiments, the refrigeration part is a thermoelectric refrigeration. In still other embodiments, the refrigeration part is an ice bag, or any other cooling materials that can reduce temperature when in contact.

In certain embodiments, the cooling device further comprises an electroacupuncture unit with at least one pair of electrodes. In some instances, the at least one pair of electrodes are connected to a low voltage electricity circuit.

In some embodiments, the cooling device further comprises a temperature controller. In other embodiments, the cooling device further comprises a controller for EA modes. In still other embodiments, the cooling device further comprises a timer to pre-set the cooling period.

In yet another aspect, the disclosed invention is directed to a method of activating brown fat in a human subject by contacting one or more regions of the neck, the supraclavicular, and the interscapular regions of the human subject with a part of a cooling device, wherein the part of the cooling device has a temperature at about 15 or less Celsius degrees; cooling the one or more regions of the neck, the supraclavicular, and the interscapular regions of the human subject for a cooling period of at least 15 minutes, thereby activating brown fat in the one or more regions of the neck, the supraclavicular, and the interscapular regions of the human subject; and performing the above two steps daily for about 14 or more days to further activate or maintain the activation status of the brown fat in the one or more regions of the neck, the supraclavicular, and the interscapular regions of the human subject.

In some embodiments of the method of activating brown fat, the part of the cooling device has a temperature ranging from about 4 to about 15 Celsius degrees. In other embodiments, the part of the cooling device has a temperature ranging from about −15 to about 4 Celsius degrees In some embodiments of the method of activating brown fat, the cooling period ranges from about 15 to about 30 minutes. In other embodiments, the cooling period ranges from about 30 minutes to about 2 hours. In still other embodiments, the cooling period ranges from about 2 to about 4 hours.

In some embodiments of the method of activating brown fat, the cooling device has a temperature controller that can be used to adjust the temperature of the part of the cooling device that contacts the human subject.

In some embodiments, the method of activating brown fat further comprises the step of applying electroacupuncture to one or more regions selected from the group consisting of the neck, the supraclavicular and the interscapular regions in the second step. In some instances, the electroacupuncture is applied simultaneously during the cooling period. In other instances, the electroacupuncture is applied prior to the cooling period. In still other instances, the electroacupuncture is applied in a period that overlaps the cooling period.

In some embodiments of the method for activating brown fat in a human subject, the cooling treatment is performed once daily for 14 or more days. In other embodiments, the cooling treatment is performed twice daily for 14 or more days. In still other embodiments, the cooling treatment is performed thrice daily for 14 or more days.

DETAILED DESCRIPTION OF THE INVENTION

Figure 1:
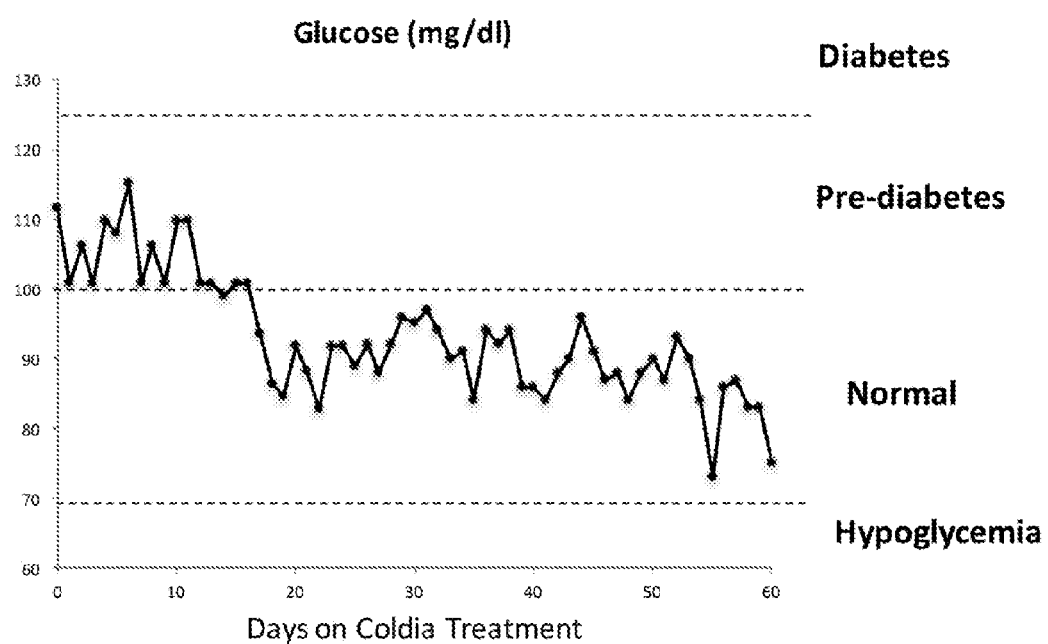
FIG. 1 shows a graph showing the normalization of impaired blood glucose by Coldia treatment. After two weeks on Coldia treatment, impaired fasting glucose was decreased to normal range (below 100 mg/dL). The regions applied ice pad felt cold at the beginning of treatment (about 10-15 minutes) during the first week of treatment. Afterwards, skin adapted to the cold and didn't feel the cold uncomfortableness. At about 2 weeks, the testing subject felt hungry more often, a typical feeling from increased energy expenditure due to BAT activation. During the last two weeks on cold treatment, EA was applied to the treated region. EA significantly increased the comfort of the treatment, and also further decreased fasting glucose.

The present disclosure is based, in part, on a new and surprising discovery that cooling certain parts of the human body under certain regimes can mitigate insulin resistance and normalize blood glucose homeostasis. Treatment methods according to the above discovery herein disclosed in the present application are referred to as "Coldia" treatments.

I. Methods for Mitigating Insulin Resistance in a Human Subject

In one aspect, the present disclosure is directed to a method of mitigating insulin resistance in a human subject. In one embodiment, the method comprises the steps of contacting one or more regions of the neck, the supraclavicular, and the interscapular regions of the human subject with a part of a cooling device with a cooling temperature at about 15 or less Celsius degrees, cooling the one or more regions of the neck, the supraclavicular, and the interscapular regions of the human subject for a cooling period of at least 15 minutes, and performing above two steps daily for about 14 or more days.

In the above embodiment, the selective location of the cooling unit on a human body prevents the unnecessary heat loss from other body regions, particularly the extremities where most of the discomfort of cold feeling comes from. Because of the selective cooling strategy, in some embodiments, the cooling temperature can go down to about −15° C. to about 4° C. Celsius degrees so as to improve the cooling efficiency without causing damage of the skin. In other embodiments, the subjects are more sensitive to cooling, the cooling temperature ranges from about 4 to about 15 Celsius degrees.

In some embodiments, the cooling temperature is set at a specific temperature during the whole treatment period. The specific temperature can be any specific temperature within the range, for example the range of about −15 to about 4 Celsius degrees, the range of about 4 to about 15 Celsius degrees, or other ranges so long as the up-limit of the temperature of about 15 Celsius degrees.

In other embodiments, the cooling temperature varies within a preset range, for example, the range of about −15 to about 4 Celsius degrees or the range of about 4 to about 15 Celsius degrees, during the treatment period. In some instances, the variation of temperature with the preset range may follow a preset program. For example, in a preset range of about −15 to about 4 Celsius degrees for a cooling period or treatment period of 2 hours, the temperature may be about −10 Celsius degree in the first hour and then zero Celsius degree in the second hour.

In some embodiments, the cooling temperature is controlled by a temperature controller that is connected to the cooling device or integrated in the cooling device. In some instances, the temperature controller may be manually controlled by a person, who may be the subject under treatment or may be a caregiver. In other instances, the temperature controller may be automatically controlled to adjust the cooling temperature according to a preset program. The temperature controller maybe digital controller with 0.1 Celsius degree resolution or mechanical controller with broader set points (1 Celsius degree or low/medium/high) known in the art.

The cooling period may vary. In some embodiments, the cooling period ranges from about 15-30 minutes. In other embodiments, the cooling period ranges from about 30 minutes to 2 hours. In still other embodiments, the cooling period ranges from about 2-4 hours.

In some embodiment, the cooling treatment may be performed once daily for 1-7 days. In some embodiments, the cooling treatment may be performed once daily for 7-14 days. In still other embodiments, the cooling treatment may be performed once daily for 14-21 days. In further embodiments, the cooling treatment may be performed once daily for more than 21 days. In some embodiments, the once daily treatment means once every 24 hour treatment. In other embodiments, the interval between two treatments may vary between 20-24 hours.

In some embodiment, the cooling treatment may be performed twice daily for 1-7 days. In some embodiments, the cooling treatment may be performed twice daily for 7-14 days. In still other embodiments, the cooling treatment may be performed twice daily for 14-21 days. In further embodiments, the cooling treatment may be performed twice daily for more than 21 days.

In a twice daily regime, the two treatments in a single day may be consecutive or not consecutive. In some embodiments, the interval between two non-consecutive treatments may be 5 minutes to an hour. In other embodiments, the interval between two non-consecutive treatments may be 1-2 hours. In still other embodiments, the interval between two non-consecutive treatments may be 2-4 hours. In still other embodiments, the interval between two non-consecutive treatments may be 4-6 hours. In still other embodiments, the interval between two non-consecutive treatments may be 6-8 hours. In still other embodiments, the interval between two non-consecutive treatments may be 8-10 hours. In still other embodiments, the interval between two non-consecutive treatments may be 10-12 hours.

In some embodiment, the cooling treatment may be performed thrice daily for 1-7 days. In some embodiments, the cooling treatment may be performed thrice daily for 7-14 days. In still other embodiments, the cooling treatment may be performed thrice daily for 14-21 days. In further embodiments, the cooling treatment may be performed thrice daily for more than 21 days. In a thrice daily regime, the three treatments in a single day may be performed consecutively or not consecutively. In some embodiment, the interval between non-consecutive treatments may vary from minutes to hours.

In some embodiments, the cooling treatment may be performed intermittently. In some instance, one may skip the cooling treatment for one day. In other instances, one may skip the cooling treatment for two consecutive days. In still other instance, one may skip the cooling treatment for three consecutive days.

In some embodiments, the cooling treatment may be performed every other day. On other embodiments, the cooling treatment may be performed once every three days. In still other embodiments, the cooling treatment may be performed once every four days. In further still other embodiments, the cooling treatment may be performed once every five days.

In some embodiments, the cooling period can be automatically set up by a timer that is connected to the cooling device. In other embodiments, the cooling period is setup by a manually controlled timer. In still other embodiments, the cooling period is not set up by a timer, but instead timed manually. The timer may be digital or mechanical with 1 minute set point known in the art.

In other embodiments, an additional step of applying electroacupuncture to one or more regions selected from the group consisting of the neck, the supraclavicular and the interscapular regions is carried out. The application of electroacupuncture may increase the insulin sensitizing efficiency of Coldia treatments and improve the comfortableness during Coldia treatments. In some instances, the additional step may be carried out during the cooling period. In other instances, the additional step may be carried out prior to the cooling period. In still other instances, the additional step may be carried out after the cooling period. In still other instances, the additional step may be carried out partially overlapping the cooling period.

The electroacupuncture may be carried out with a separate electroacupuncture device that is known in the art. Alternatively, the electroacupuncture may be integrated within the cooling device. In some embodiments, the electroacupuncture device may be those as disclosed in the present disclosure as described below.

II. Methods for Preventing, Delaying or Treating Type 2 Diabetes in a Human Subject In another aspect, the present disclosure is directed to a method of preventing, delaying or treating type 2 diabetes in a human subject. In one embodiment, the method comprises the steps of contacting one or more regions of the neck, the supraclavicular, and the interscapular regions of the human subject with a part of a cooling device with a cooling temperature at about 15 or less Celsius degrees, cooling the one or more regions of the neck, the supraclavicular, and the interscapular regions of the human subject for a cooling period of at least 15 minutes, and performing above two steps daily for about 14 or more days.

In the above embodiment, the selective location of the cooling unit on a human body prevents the unnecessary heat loss from other body regions, particularly the extremities where most of the discomfort of cold feeling comes from. Because of the selective cooling strategy, in some embodiments, the cooling temperature can go down to about −15° C. to about 4° C. Celsius degrees so as to improve the cooling efficiency without causing damage of the skin. In other embodiments, the subjects are more sensitive to cooling, the cooling temperature ranges from 4 to 15 Celsius degrees.

In some embodiments, the cooling temperature is set at a specific temperature during the whole treatment period. The specific temperature can be any specific temperature within the range, for example the range of about −15 to about 4 Celsius degrees, the range of about 4 to about 15 Celsius degrees, or other ranges so long as the up-limit of the temperature of about 15 Celsius degrees.

In other embodiments, the cooling temperature varies within a preset range, for example, for example the range of about −15 to about 4 Celsius degrees or the range of about 4 to about 15 Celsius degrees, during the treatment period. In some instances, the variation of temperature with the preset range may follow a preset program. For example, in a preset range of about −15 to about 4 Celsius degrees for a cooling period or treatment period of 2 hours, the temperature may be about −10 Celsius degree in the first hour and then zero Celsius degree in the second hour.

In some embodiments, the cooling temperature is controlled by a temperature controller that is connected to the cooling device or integrated in the cooling device. In some instances, the temperature controller may be manually controlled by a person, who may be the subject under treatment or may be a caregiver. In other instances, the temperature controller may be automatically controlled to adjust the cooling temperature according to a preset program. The temperature controller may be a digital controller with 0.1 Celsius degree resolution or mechanical controller with broader set points (1 Celsius degree or low/medium/high) known in the art.

The cooling period may vary. In some embodiments, the cooling period ranges from about 15-30 minutes. In other embodiments, the cooling period ranges from 30 minutes to 2 hours. In still other embodiments, the cooling period ranges from about 2-4 hours.

In some embodiment, the cooling treatment may be performed once daily for 1-7 days. In some embodiments, the cooling treatment may be performed once daily for 7-14 days. In still other embodiments, the cooling treatment may be performed once daily for 14-21 days. In further embodiments, the cooling treatment may be performed once daily for more than 21 days. In some embodiments, the once daily treatment means once every 24 hour treatment. In other embodiments, the interval between two treatments may vary between 20-24 hours.

In some embodiment, the cooling treatment may be performed twice daily for 1-7 days. In some embodiments, the cooling treatment may be performed twice daily for 7-14 days. In still other embodiments, the cooling treatment may be performed twice daily for 14-21 days. In further embodiments, the cooling treatment may be performed twice daily for more than 21 days.

In a twice daily regime, the two treatments in a single day may be consecutive or not consecutive. In some embodiments, the interval between two non-consecutive treatments may be 5 minutes to an hour. In other embodiments, the interval between two non-consecutive treatments may be 1-2 hours. In still other embodiments, the interval between two non-consecutive treatments may be 2-4 hours. In still other embodiments, the interval between two non-consecutive treatments may be 4-6 hours. In still other embodiments, the interval between two non-consecutive treatments may be 6-8 hours. In still other embodiments, the interval between two non-consecutive treatments may be 8-10 hours. In still other embodiments, the interval between two non-consecutive treatments may be 10-12 hours.

In some embodiment, the cooling treatment may be performed thrice daily for 1-7 days. In some embodiments, the cooling treatment may be performed thrice daily for 7-14 days. In still other embodiments, the cooling treatment may be performed thrice daily for 14-21 days. In further embodiments, the cooling treatment may be performed thrice daily for more than 21 days. In a thrice daily regime, the three treatments in a single day may be performed consecutively or not consecutively. In some embodiment, the interval between non-consecutive treatments may vary from minutes to hours.

In some embodiments, the cooling treatment may be performed intermittently. In some instance, one may skip the cooling treatment for one day. In other instances, one may skip the cooling treatment for two consecutive days. In still other instance, one may skip the cooling treatment for three consecutive days.

In some embodiments, the cooling treatment may be performed every other day. On other embodiments, the cooling treatment may be performed once every three days. In still other embodiments, the cooling treatment may be performed once every four days. In further still other embodiments, the cooling treatment may be performed once every five days.

In some embodiments, the cooling period can be automatically set up by a timer that is connected to the cooling device. In other embodiments, the cooling period is setup by a manually controlled timer. In still other embodiments, the cooling period is not set up by a timer, but instead timed manually. The timer may be digital or mechanical with 1 minute set point known in the art.

In other embodiments, an additional step of applying electroacupuncture to one or more regions selected from the group consisting of the neck, the supraclavicular and the interscapular regions is carried out. The application of electroacupuncture may increase the insulin sensitizing efficiency of Coldia treatments and improve the comfortableness during Coldia treatments. In some instances, the additional step may be carried out during the cooling period. In other instances, the additional step may be carried out prior to the cooling period. In still other instances, the additional step may be carried out after the cooling period. In still other instances, the additional step may be carried out partially overlapping the cooling period.

The electroacupuncture may be carried out with a separate electroacupuncture device that is known in the art. Alternatively, the electroacupuncture may be integrated within the cooling device. In some embodiments, the electroacupuncture device may be those as disclosed in the present disclosure as described below.

III. Methods for Activating Brown Fat without Incurring a Sympathetic Nerve-Mediated Cold Feeling in a Human Subject In another aspect, the present disclosure is directed to a method of activating brown fat without incurring a sympathetic nerve-mediated cold feeling in a human subject.

Coldness is the classic activator of BAT and the nature of BAT is to generate heat to defend body temperature during cold environment. It involves multiple processes coordinated with different organs: skin sensing of the cold, sympathetic neuronal stimulation, brown adipocyte activation, blood flow increase to the activated region (8-10). Coldness activates the whole spectrum of pathways in multiple types of cells, including brown adipocytes themselves, endothelial cells for vascularization, neurons for innervation and immune cells (11-13).

The alternatives to activate BAT is by pharmacological reagents that the scientific community and pharmaceutical industry spend billions of dollars on (14). There are some potent browning candidates identified over the past decade from in vitro screening or rodent studies, however their effectiveness in humans and safety concerns restrict their clinical applications (15). For example, the major class of BAT activators, β-adrenergic receptor agonists, robustly activates BAT in mice but works poorly in humans (16, 17). Thyroid hormones activate BAT efficiently and it is naturally synthesized in humans, however, its safety should be closely watched due to overdosing lethality (18, 19). The insulin-sensitizing FGF21 and TZDs induces BAT activity but also cause bone loss (4, 20). The angiongenic factor VEGF-A is able to induce browning in mice (21) but its obvious cancer risks dampen its therapeutic potential (22).

Comparing to all of these pharmacological reagents, coldness has a unique advantage, the safety. It decreases heart rate and blood pressure rather than the increase of cardiovascular risks, improves bone and muscle health rather than fracture, and has no risks for cancer. Moreover, any chemical or biological reagent to activate BAT has to consider dose and clearance time to treat humans, but these problems do not exist for coldness-induced BAT activation. Therefore, coldness represents the most efficient but least expensive, natural and safe approach to activate BAT.

Cold approaches to humans presently include immersing a limb into icy water, staying in climate-controlled rooms or water-circulating incubator. These approaches are completely dependent on cold feeling-stimulated sympathetic nerve activity. However, none of these approaches can be applied to free-living individuals or is practically operational. And it is unrealistic to treat patients with coldness because of the uncomfortableness although cold prescription has been suggested to treat obesity and diabetes (13).

The Coldia treatment is different from the traditional way of activating BAT, which depends on the sympathetic nerve mediated cold feeling. Adipocyte can directly sense the coldness and activate thermogenic response (23). The Coldia treatment disclosed in the present application directly stimulates the BAT around one or more regions of neck, supraclavicular and interscapular regions without causing the unnecessary cold feeling from non-BAT regions, particularly the extremities where most of the uncomfortableness come from.

In one embodiment, the method comprises the steps of contacting one or more regions of the neck, the supraclavicular, and the interscapular regions of the human subject with a part of a cooling device with a cooling temperature at about 15 or less Celsius degrees, cooling the one or more regions of the neck, the supraclavicular, and the interscapular regions of the human subject for a cooling period of at least 15 minutes, and performing above two steps daily for about 14 or more days.

In the above embodiment, the selective location of the cooling unit on a human body prevents the unnecessary heat loss from other body regions, particularly the extremities where most of the discomfort of cold feeling comes from. Because of the selective cooling strategy, in some embodiments, the cooling temperature can go down to about −15° C. to about 4° C. Celsius degrees so as to improve the cooling efficiency without causing damage of the skin. In other embodiments, the subjects are more sensitive to cooling, the cooling temperature ranges from about 4 to about 15 Celsius degrees.

In some embodiments, the cooling temperature is set at a specific temperature during the whole treatment period. The specific temperature can be any specific temperature within the range, for example the range of about −15 to about 4 Celsius degrees, the range of about 4 to about 15 Celsius degrees, or other ranges so long as the up-limit of the temperature of about 15 Celsius degrees.

In other embodiments, the cooling temperature varies within a preset range, for example, for example the range of about −15 to about 4 Celsius degrees or the range of about 4 to about 15 Celsius degrees, during the treatment period. In some instances, the variation of temperature with the preset range may follow a preset program. For example, in a preset range of about −15 to about 4 Celsius degrees for a cooling period or treatment period of 2 hours, the temperature may be about −10 Celsius degree in the first hour and then zero Celsius degree in the second hour.

In some embodiments, the cooling temperature is controlled by a temperature controller that is connected to the cooling device or integrated in the cooling device. In some instances, the temperature controller may be manually controlled by a person, who may be the subject under treatment or may be a caregiver. In other instances, the temperature controller may be automatically controlled to adjust the cooling temperature according to a preset program. The temperature controller may be a digital controller with 0.1 Celsius degree resolution or mechanical controller with broader set points (1 Celsius degree or low/medium/high) known in the art.

The cooling period may vary. In some embodiments, the cooling period ranges from 15-30 minutes. In other embodiments, the cooling period ranges from 30 minutes to 2 hours. In still other embodiments, the cooling period ranges from 2-4 hours.

In some embodiment, the cooling treatment may be performed once daily for 1-7 days. In some embodiments, the cooling treatment may be performed once daily for 7-14 days. In still other embodiments, the cooling treatment may be performed once daily for 14-21 days. In further embodiments, the cooling treatment may be performed once daily for more than 21 days. In some embodiments, the once daily treatment means once every 24 hour treatment. In other embodiments, the interval between two treatments may vary between 20-24 hours.

In some embodiment, the cooling treatment may be performed twice daily for 1-7 days. In some embodiments, the cooling treatment may be performed twice daily for 7-14 days. In still other embodiments, the cooling treatment may be performed twice daily for 14-21 days. In further embodiments, the cooling treatment may be performed twice daily for more than 21 days.

In a twice daily regime, the two treatments in a single day may be consecutive or not consecutive. In some embodiments, the interval between two non-consecutive treatments may be 5 minutes to an hour. In other embodiments, the interval between two non-consecutive treatments may be 1-2 hours. In still other embodiments, the interval between two non-consecutive treatments may be 2-4 hours. In still other embodiments, the interval between two non-consecutive treatments may be 4-6 hours. In still other embodiments, the interval between two non-consecutive treatments may be 6-8 hours. In still other embodiments, the interval between two non-consecutive treatments may be 8-10 hours. In still other embodiments, the interval between two non-consecutive treatments may be 10-12 hours.

In some embodiment, the cooling treatment may be performed thrice daily for 1-7 days. In some embodiments, the cooling treatment may be performed thrice daily for 7-14 days. In still other embodiments, the cooling treatment may be performed thrice daily for 14-21 days. In further embodiments, the cooling treatment may be performed thrice daily for more than 21 days. In a thrice daily regime, the three treatments in a single day may be performed consecutively or not consecutively. In some embodiment, the interval between non-consecutive treatments may vary from minutes to hours.

In some embodiments, the cooling treatment may be performed intermittently. In some instance, one may skip the cooling treatment for one day. In other instances, one may skip the cooling treatment for two consecutive days. In still other instance, one may skip the cooling treatment for three consecutive days.

In some embodiments, the cooling treatment may be performed every other day. On other embodiments, the cooling treatment may be performed once every three days. In still other embodiments, the cooling treatment may be performed once every four days. In further still other embodiments, the cooling treatment may be performed once every five days.

In some embodiments, the cooling period can be automatically set up by a timer that is connected to the cooling device. In other embodiments, the cooling period is setup by a manually controlled timer. In still other embodiments, the cooling period is not set up by a timer, but instead timed manually. The timer may be digital or mechanical with 1 minute set point known in the art.

In other embodiments, an addition step of applying electroacupuncture to one or more regions selected from the group consisting of the neck, the supraclavicular and the interscapular regions is carried out. The application of electroacupuncture may increase the insulin sensitizing efficiency of Coldia treatments and improve the comfortableness during Coldia treatments. In some instances, the additional step may be carried out during the cooling period. In other instances, the additional step may be carried out prior to the cooling period. In still other instances, the additional step may be carried out after the cooling period. In still other instances, the additional step may be carried out partially overlapping the cooling period.

The electroacupuncture may be carried out with a separate electroacupuncture device that is known in the art. Alternatively, the electroacupuncture may be integrated within the cooling device. In some embodiments, the electroacupuncture device may be those as disclosed in the present disclosure as described below.

IV. Cooling Devices

In another aspect, the present disclosure is directed to a cooling device. In some embodiments, the cooling device is an ice pad or other similar cooling materials, which can be directly applied to cool desired body regions.

In other embodiments, the cooling device comprises a body-contacting vest that directly contacts one or more regions of the neck, the supraclavicular and the interscapular regions, a tube that is filled with cooling media and partially contacts the body-contacting vest, and a refrigeration part that cools the cooling media in the tube, which cooling media in turn cools the body-contacting vest to a specified temperature of 15 Celsius degree or below.

In some embodiments, the body-contacting vest is made to fit the neck, the supraclavicular and the interscapular regions. In other embodiments, the body-contacting vest is made to fit one or more regions of the neck regions only. In still other embodiments, the body-contacting vest is made to fit the supraclavicular regions only. In still other embodiments, the body-contacting vest is made to fit the interscapular regions only. In still other embodiments, the body-contacting vest is made to fit the neck and the supraclavicular regions only. In still other embodiments, the body-contacting vest is made to fit the neck and the interscapular regions only. In still other embodiments, the body-contacting vest is made to fit the supraclavicular and the interscapular regions only.

In some embodiments, the body-contacting vest is made of fabric. The fabric can be a fabric known in the art. In other embodiments, the body-contacting vest is made of carbon fibers. In still other embodiments, the body-contacting vest is made of metal. In the body-contacting vest may be cooled to a temperature range of about −15 to about 15 Celsius degrees.

In some embodiments, the refrigeration part is a cyclic refrigeration. The cyclic refrigeration can be any refrigeration system with sufficient power to lower the temperature of cooling media to a designed range. The cooling media or fluid circulates between refrigeration system and cooling tube. In some instances, the cooling media or fluid may be salted water, or any other low melting temperature fluid. The electricity circuit for compressor may be separated from those used for other parts of the cooling device.

In other embodiments, the refrigeration part is a thermoelectric refrigeration system. In some embodiments, the cooling side of the thermoelectric refrigeration system may face the skin and applied directly to the vest without the need for the tube and cooling media.

In some embodiments, the cooling device further comprises an electroacupuncture unit with at least one pair of electrodes. In some embodiments, the electrodes are implanted in the cooling device. The electrodes may be low voltage electricity circuit, which is separated from the circuit for refrigeration system. An exemplary electroacupuncture device has the parameters shown in Table 1.

TABLE 1

Exemplary EA

| | |
|---|---|
| Output: | DC 5-9 V |
| Wave form: | Pulse and biphasic |
| Pulse duration: | 100 μs |
| Frequency: | <70 Hz, with 0.01-1 Hz modulating frequency |
| Pulse period: | 10-850 miliseconds |
| Output current: | 0-125 milliamps |
| Output voltage range: | 7-85 V (@ 500-10k Ω) |
| Wave shape: | rectangular |

In some embodiments, the cooling device further comprises a controller for EA modes. Examples of such controller may be a digital controller with 0.1 Celsius degree resolution or mechanical controller with broader set points (1 Celsius degree or low/medium/high) known in the art.

In some embodiments, the cooling device further comprises a timer to pre-set the cooling period. Examples of such timer may be a digital or mechanical timer with 1 minute set point known in the art.

In some embodiments, the cooling device may be a mobile device that can be used at home or at work. In some instance, the power for the mobile cooling device may be supplied via wire electricity. In other instances, the power may be supplied by a rechargeable battery. In some instances, the mobile cooling device may be wearable and thus there is no need for the human subject to maintain a certain position during the treatment. In some further instances, the mobile cooling device may also be applied at ambient temperature room without staying in a cold environment during the treatment.

In other embodiments, the cooling device may be a stationary device. In some instances, the stationary cooling device may comprise an integrated electricity-powered refrigeration system together with cooling tubes and cooling vest, which is further incorporated with EA. In other instances, the stationary cooling device may further comprise heart monitor system, insulin sensitivity measuring and entertaining system. Stationary cooling devices may be preferably used in hospital or rehabilitation centers.

As used in this application, including the appended claims, the term "about," particularly in reference to a given quantity, is meant to encompass deviations of plus or minus ten percent.

As used herein, the singular forms "a," "an," and "the" include plural references, unless the content clearly dictates otherwise, and are used interchangeably with "at least one" and "one or more."

As used herein, the terms "comprises," "comprising," "includes," "including," "contains," "containing," and any variations thereof, are intended to cover a non-exclusive inclusion, such that a process, method, product-by-process, or composition of matter that comprises, includes, or contains an element or list of elements does not include only those elements but can include other elements not expressly listed or inherent to such process, method, product-by-process, or composition of matter.

As used herein, the term "resistance" as used in insulin resistance, means that the subject does not show a response to a substance based on an underlying ability of cells to escape the effect of the substance. Resistance includes de novo resistance and acquired resistance. A human subject that exhibit de novo resistance do not respond to the substance from the start. However, in acquired resistance, the cells initially respond to a substance but eventually acquire resistance to it. The cells might also show cross-resistance to other structurally and mechanistically unrelated substance—a phenomenon commonly known as multi drug resistance (MDR). Owing to acquisition of MDR, treatment regimens that combine multiple agents with different targets are no longer effective.

EXAMPLES

1. Normalization of Impaired Blood Glucose by Coldia Treatment.

The example describes the use of the Coldia treatment in the normalization of impaired blood glucose homeostasis in a human subject with insulin resistance. Specifically, a healthy male who has insulin resistance and impaired fasting glucose levels underwent the Coldia treatment. Ice pads were used as a cooling device in this example. Ice pads were directly applied to the neck, the supraclavicular, and the interscapular regions of the human subject for a duration of two hours daily. The treatment lasted for 60 days, during which time the human subject maintained his normal workouts and diets. Fasting glucose levels were measured every morning. Fasting glucose levels are indications for insulin resistance and the diagnosis of type II diabetes.

As shown in FIG. 1, when the Coldia treatment started, the human subject is in a pre-diabetes status with fasting glucose levels above 100 mg/dl. About 14 days after the Coldia treatment, the fasting glucose levels fell below 100 mg/dl and stayed below 100 mg/dl during the whole remaining treatment period to day 60. The Coldia treatment in a human subject with insulin resistance therefore can result in the normalization of impaired blood glucose homeostasis, which may improve insulin sensitivity, delay or prevent the onset of hyperglycemia and diabetes, reduce the severity or even cure diabetes and the associated co-morbidities, including dyslipidemia, cardiovascular risks.

2. Maintenance of the Normal Blood Glucose Levels after Coldia Treatment.

Figure 2:
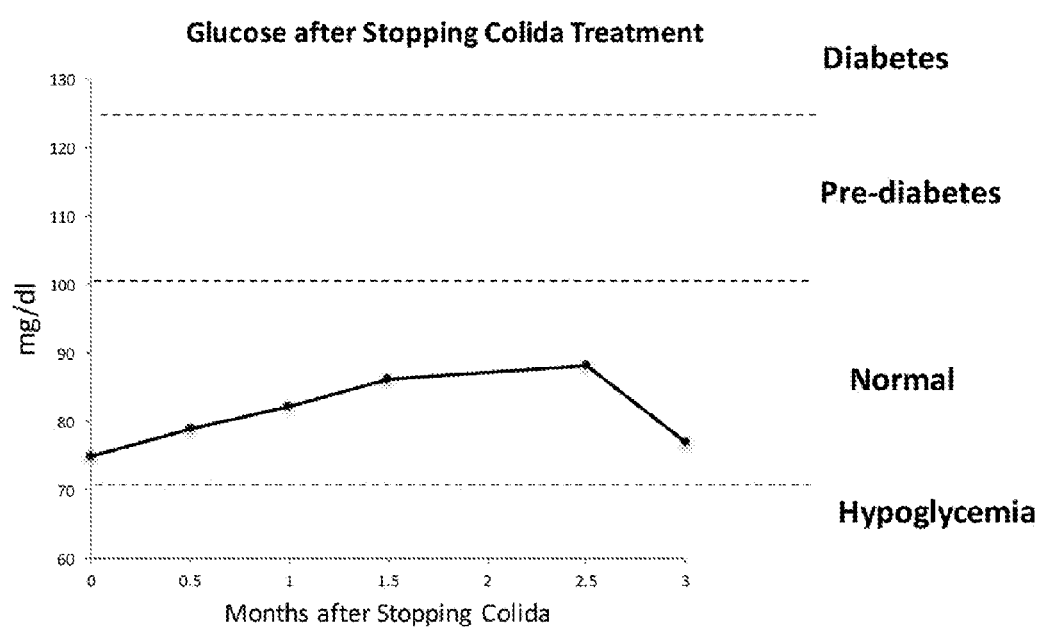
FIG. 2 shows a plot depicting that the normal blood glucose levels were maintained after Coldia treatment. Fasting blood glucose was monitored for three months after stopping Coldia treatment. The benefit of decreasing fasting glucose from Coldia treatment was maintained for at least 3 months.

This example describes that the fasting glucose levels stay in the normal range in a human subject with insulin resistance even after the Coldia treatment is stopped in the human subject. Specifically, following the Coldia treatment in Example A, the fasting glucose was monitored for another three months post-treatment. As shown in FIG. 2, the fasting glucose from Coldia treatment was maintained in the normal range for 3 months.

3. A Cooling Device for the Coldia Treatment.

Figure 3:
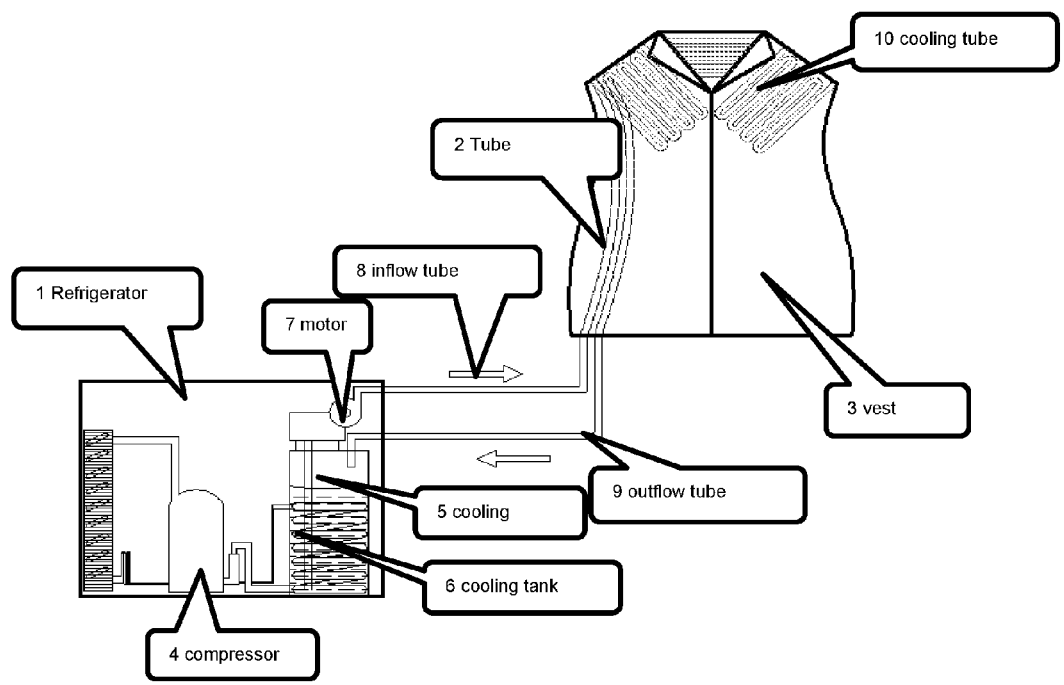
FIG. 3 shows an exemplary cooling device for the Coldia treatment. The cooling fluid in the tank is cooled down by compressor refrigeration, and then pumped to the cooling vest through a tube by a motor. The cooling fluid takes heat away from targeted body area and is circulated back to the tank.

This example describes one embodiment of the cooling device that can be used for the Coldia treatment. As shown in FIG. 3, the cooling device comprises a refrigerator 1, the tube 2, and the vest 3. The refrigerator 1 comprises a compressor 4, a cooling tank 6, and a motor 7. The compressor 4 is used for active cooling. The exemplary compressor has the parameters shown in Table 2. The cooling media 5 in the cooling tank 6 is cooled down by compressor refrigeration, and then pumped to the cooling tube 10 via the inflow tube 8 by the motor 7. The cooling media 5 in the cooling tube 10 cools the part of the vest 3 that contacts the cooling tube 10. The cooled vest 3 directly contacts the targeted body regions. As a result, the cooling media takes heat away from the targeted body regions and is circulated back to the cooling tank 6 through the outflow tube 9.

TABLE 2

Parameters of a compressor.

| Compressor model | CW-5300 |
|---|---|
| Voltage | 220 VAC |
| Output watt | 0.75 KW |
| Compressor watt | 1.67 KW |
| coolant | R-134a |
| Cooling fluid | ethylene glycol |
| Fluid volume | 9 L |
| Temperature | 5-25° C. |
| Temp. Accurancy | ±0.3° C. |

4. Improved Glucose Homeostasis and Insulin Sensitivity after Coldia Treatment.

This example describes additional embodiments of Coldia treatment to improve glucose homeostasis and insulin sensitivity. Specifically, two newly identified insulin resistant patients (1 male, 1 female) received Coldia treatment (2 hours daily) for 8 weeks. Specifically, in this particular Coldia treatment, a cooling vest with ice pads was used to cover and cool the neck, supraclavicular, and interscapular regions once daily for 8 weeks. Each cooling treatment lasted for about 2 hours. EA was performed concurrently with the cooling treatment in the first 30 minutes of each cooling treatment.

Diabetes-related tests were performed before and after the treatment. The test results are shown in Table 3 below.

In both patients, BMIs were slightly decreased after 8-weeks Coldia treatment, from 25.6 to 24.93 and 24.13 to 23.34 respectively. HOMA-IR was significantly improved, from 5.67 to 3.88 and 8.35 to 5.79 in the two patients, respectively.

Figure 4:
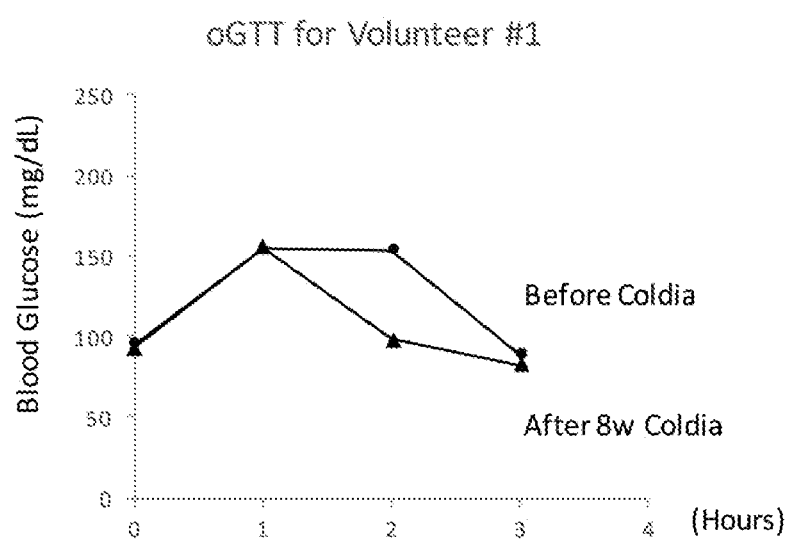
FIG. 4 shows a plot depicting the results of oral glucose tolerance testing in patient #1 before and after Coldia treatment for 8 weeks. The x-axis shows the time points when blood glucose concentration was measured.
Figure 5:
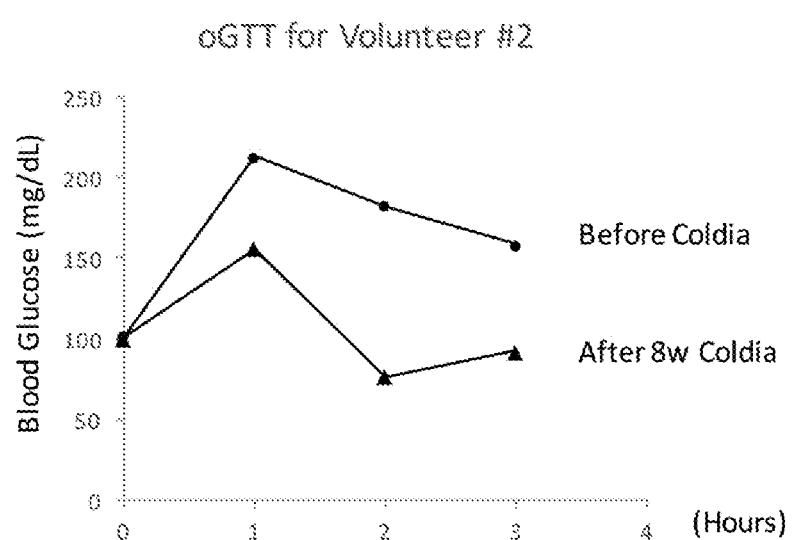
FIG. 5 shows a plot depicting the results of oral glucose tolerance testing in patient #2 before and after Coldia treatment for 8 weeks. The x-axis shows the time points when blood glucose concentration was measured.

In both patients, glucose intolerance was completely normalized after the treatment. As shown in FIG. 4, the glucose level at 2 hours post glucose administration were normalized from 8.53 to 5.45 in patient #1. FIG. 5 shows that the glucose level at 2 hours post glucose administration were normalized from 10.16 to 4.27 in patient #2.

Figure 6:
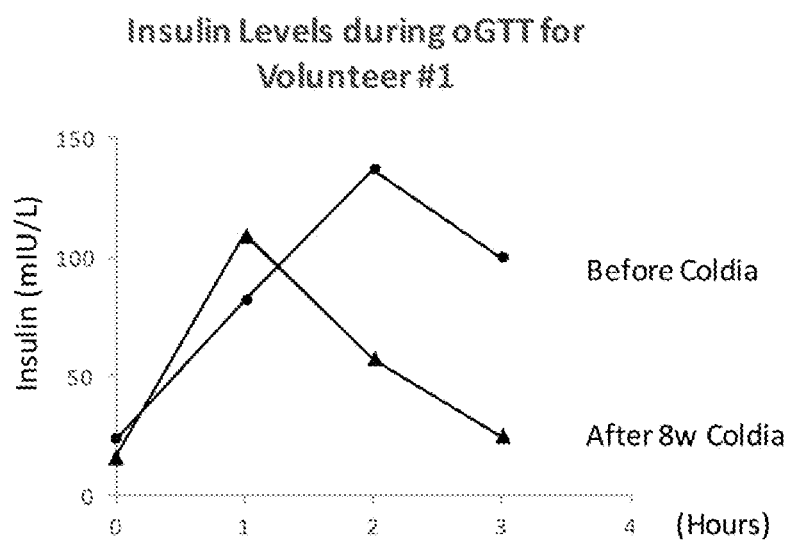
FIG. 6 shows a plot depicting the results of insulin level testing during the same period of oral glucose tolerance testing as in FIG. 4 in patient #1 before and after Coldia treatment for 8 weeks. The x-axis shows the time points when blood insulin concentration was measured.
Figure 7:
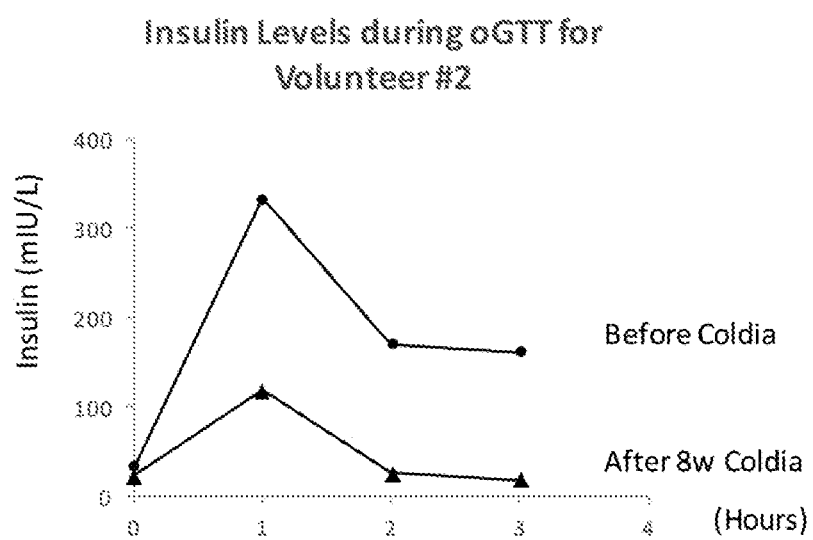
FIG. 7 shows a plot depicting the results of insulin level testing during the same period of oral glucose tolerance testing as in FIG. 5 in patient #2 before and after Coldia treatment for 8 weeks. The x-axis shows the time points when blood insulin concentration was measured.

In addition, the insulin release during oral glucose tolerance was also significantly decreased in both patients. As shown in FIG. 6, the 2 hr insulin and 3 hr insulin in patient #1 were reduced from 136.8 to 57.3 and from 99.9 to 24.9, respectively. As shown in FIG. 7. the 2 hr insulin and 3 hr insulin in patient #2 were reduced from 171.2 to 25.7, and from 162.2 to 18.3, respectively. These data showed improvement of insulin sensitivity and beta-cell function in both patients.

Coldia treatment did not affect heart functions and liver lipid metabolism as there is no significant changes of blood pressure, hear rate, Triglycerides, LDL-C or HDL-C. See Table 3. This example showed that Coldia treatment for 8 weeks significantly improved glucose homeostasis and insulin sensitivity, and even cured early stage type 2 diabetes. Therefore, Coldia treatment can be an efficient way to manage diabetes.

TABLE 3

Testing results after Coldia treatment for eight weeks.

| | Normal Range | Patient #1 | | Patient #2 | |
|---|---|---|---|---|---|
| Age | | 55 | | 49 | |
| Sex | | Male | | Female | |
| Treatment Time | | 0W | 8W | 0W | 8W |
| Body Weight (kg) | | 81 | 79 | 61 | 59 |
| Height (m) | | 1.78 | 1.78 | 1.59 | 1.59 |
| BMI (kg/m$^2$) | | 25.6 | 24.93 | 24.13 | 23.34 |
| Waist Circumference (cm) | | 97 | 97 | 83 | 82 |
| Hip Circumference (cm) | | 104 | 102 | 97 | 100 |
| Waist-Hip Ratio | | 0.93 | 0.95 | 0.86 | 0.82 |
| Glucose Control and Insulin Resistance | | | | | |
| HOMA-IR (Fasting Glucose x Fasting Insulin/22.5) | <2.5 | 5.67 | 3.88 | 8.35 | 5.79 |
| HbA1c (%) | 4-6 | 5.8 | | 6.2 | 5.9 |
| Fasting Glucose (mmol/L) | 3.9-6.1 | 5.32 | 5.17 | 5.62 | 5.61 |
| 1 hour Oral Glucose Tolerance (mmol/L) | | 8.56 | 8.61 | 11.83 | 8.69 |
| 2 hour Oral Glucose Tolerance (mmol/L) | <7.8 | 8.53 | 5.45 | 10.16 | 4.27 |
| 3 hour Oral Glucose Tolerance (mmol/L) | | 4.93 | 4.58 | 8.82 | 5.14 |
| Fasting Insulin (mIU/L) | 5.0-25.0 | 24.0 | 16.8 | 33.3 | 23.1 |
| 1 hr Insulin (mIU/L) | | 81.9 | 109.1 | 333.8 | 118.0 |
| 2 hr Insulin (mIU/L) | | 136.8 | 57.3 | 171.2 | 25.7 |
| 3 hr Insulin (mIU/L) | | 99.9 | 24.9 | 162.2 | 18.3 |
| Cardiovascular Function | | | | | |
| Blood Pressure Systolic/Diastolic (mmHg) | | 120/90 | 132/85 | 116/78 | 120/63 |
| Heart Rate (bmp) | | 76 | 80 | 60 | 63 |
| Lipids | | | | | |
| Triglycerides (mmol/L) | 0.56-1.47 | 1.86 | 1.75 | 4.40 | 5.40 |
| LDL-C (mmol/L) | 2.7-3.1 | 4.02 | 3.45 | 2.66 | 3.22 |
| HDL-C (mmol/L) | 1.29-1.55 | 1.12 | 1.06 | 0.65 | 0.78 |

REFERENCE

1. WHO. Obesity: preventing and managing the global epidemic. Report of a WHO consultation. *World Health Organization technical report series.* 2000; 894:i-xii, 1-253.
2. Stevens G A, Singh G M, Lu Y, Danaei G, Lin J K, Finucane M M, et al. National, regional, and global trends in adult overweight and obesity prevalences. *Population health metrics.* 2012; 10(1):22.
3. CDC. National Diabetes Statistics Report: Estimates of Diabetes and Its Burden in the United States, 2014. *US Department of Health and Human Services.* 2014.
4. Ahmadian M, Suh J M, Hah N, Liddle C, Atkins A R, Downes M, et al. PPARgamma signaling and metabolism: the good, the bad and the future. *Nat Med.* 2013; 19(5): 557-66.
5. Stein S A, Lamos E M, and Davis S N. A review of the efficacy and safety of oral antidiabetic drugs. *Expert opinion on drug safety.* 2013; 12(2):153-75.
6. Lee P, Smith S, Linderman J, Courville A B, Brychta R J, Dieckmann W, et al. Temperature-acclimated brown adipose tissue modulates insulin sensitivity in humans. *Diabetes.* 2014; 63(11):3686-98.
7. Hanssen M J, Hoeks J, Brans B, van der Lans A A, Schaart G, van den Driessche J J, et al. Short-term cold acclimation improves insulin sensitivity in patients with type 2 diabetes mellitus. *Nat Med.* 2015; 21(8):863-5.

8. Cannon B, and Nedergaard J. Brown adipose tissue: function and physiological significance. *Physiological reviews.* 2004; 84(1):277-359.
9. Cannon B, Houstek J, and Nedergaard J. Brown adipose tissue. More than an effector of thermogenesis? *Ann NY Acad Sci.* 1998; 856:171-87.
10. Cannon B, Shabalina I G, Kramarova T V, Petrovic N, and Nedergaard J. Uncoupling proteins: a role in protection against reactive oxygen species—or not? *Biochim Biophys Acta.* 2006; 1757(5-6):449-58.
11. Kajimura S, Seale P, and Spiegelman B M. Transcriptional control of brown fat development. *Cell Metab.* 2010; 11(4):257-62.
12. Rosen E D, and Spiegelman B M. What we talk about when we talk about fat. *Cell.* 2014; 156(1-2):20-44.
13. Harms M, and Seale P. Brown and beige fat: development, function and therapeutic potential. *Nat Med.* 2013; 19(10):1252-63.
14. Wu J, Cohen P, and Spiegelman B M. Adaptive thermogenesis in adipocytes: is beige the new brown? *Genes Dev.* 2013; 27(3):234-50.
15. Cypess A M, Haft C R, Laughlin M R, and Hu H H. Brown fat in humans: consensus points and experimental guidelines. *Cell Metab.* 2014; 20(3):408-15.
16. Buemann B, Toubro S, and Astrup A. Effects of the two beta3-agonists, ZD7114 and ZD2079 on 24 hour energy expenditure and respiratory quotient in obese subjects. *Int J Obes Relat Metab Disord.* 2000; 24(12):1553-60.
17. Arch J R. beta(3)-Adrenoceptor agonists: potential, pitfalls and progress. *European journal of pharmacology.* 2002; 440(2-3):99-107.
18. Mullur R, Liu Y Y, and Brent G A. Thyroid hormone regulation of metabolism. *Physiological reviews.* 2014; 94(2):355-82.
19. Chen W, Yang Q, and Roeder R G. Dynamic interactions and cooperative functions of PGC-lalpha and MED1 in TRalpha-mediated activation of the brown-fat-specific UCP-1 gene. *Molecular cell.* 2009; 35(6):755-68.
20. Wei W, Dutchak P A, Wang X, Ding X, Wang X, Bookout A L, et al. Fibroblast growth factor 21 promotes bone loss by potentiating the effects of peroxisome proliferator-activated receptor gamma. *Proc Natl Acad Sci USA.* 2012; 109(8):3143-8.
21. Sun K, Kusminski C M, Luby-Phelps K, Spurgin S B, An Y A, Wang Q A, et al. Brown adipose tissue derived VEGF-A modulates cold tolerance and energy expenditure. *Molecular metabolism.* 2014; 3(4):474-83.
22. Goel H L, and Mercurio A M. VEGF targets the tumour cell. Nature reviews *Cancer.* 2013; 13(12):871-82.
23. Ye L, Wu J, Cohen P, Kazak L, Khandekar M J, Jedrychowski M P, et al. Fat cells directly sense temperature to activate thermogenesis. *Proc Natl Acad Sci USA.* 2013; 110(30):12480-5.

I claim:

1. A method for mitigating insulin resistance in a human subject, comprising:
   a. contacting one or more regions of neck, supraclavicular, and interscapular regions of the human subject with a part of a cooling device, wherein the part of the cooling device has a temperature at about 15 or less Celsius degrees;
   b. cooling the one or more regions of neck, supraclavicular, and interscapular regions of the human subject for a cooling period of at least 15 minutes and applying electroacupuncture to one or more regions selected from the group consisting of the neck, the supraclavicular and the interscapular regions; and
   c. performing steps a and b for one or more times daily for about 14 or more days.

2. The method of claim 1, wherein the part of the cooling device has a temperature ranging from about 4 to about 15 Celsius degrees.

3. The method of claim 1, wherein the part of the cooling device has a temperature ranging from about −15 to about 4 Celsius degrees.

4. The method of claim 1, wherein the cooling period ranges from about 15 to about 30 minutes.

5. The method of claim 1, wherein the cooling period ranges from about 30 minutes to about 2 hours.

6. The method of claim 1, wherein the cooling period ranges from about 2 to about 4 hours.

7. The method of claim 1, wherein the cooling device has a temperature controller that can be used to adjust the temperature of the part of the cooling device that contacts the human subject.

8. The method of claim 1, wherein the electroacupuncture is applied simultaneously during the cooling period.

9. The method of claim 1, wherein the electroacupuncture is applied prior to the cooling period.

10. The method of claim 1, wherein the electroacupuncture is applied in a period that overlaps the cooling period.

11. The method of claim 1, wherein in the step c, the steps a and b are performed once daily for 14 or more days.

12. The method of claim 1, wherein in the step c, the steps a and b are performed twice daily for 14 or more days.

13. The method of claim 1, wherein in the step c, the steps a and b are performed thrice daily for 14 or more days.

14. A method for preventing, delaying or treating type 2 diabetes in a human subject, comprising:
   a. contacting one or more regions of neck, supraclavicular, and interscapular regions of the human subject with a part of a cooling device, wherein the part of the cooling device has a temperature at about 15 or less Celsius degrees;
   b. cooling the one or more regions of the neck, the supraclavicular, and the interscapular regions of the human subject for a cooling period of at least 15 minutes and applying electroacupuncture to one or more regions selected from the group consisting of the neck, the supraclavicular and the interscapular regions; and
   c. performing steps a and b for one or more times daily for about 14 or more days.

15. The method of claim 14, wherein the part of the cooling device has a temperature ranging from about 4 to about 15 Celsius degrees.

16. The method of claim 14, wherein the part of the cooling device has a temperature ranging from about −15 to about 4 Celsius degrees.

17. The method of claim 14, wherein the cooling period ranges from about 15 to about 30 minutes.

18. The method of claim 14, wherein the cooling period ranges from about 30 minutes to about 2 hours.

19. The method of claim 14, wherein the cooling period ranges from about 2 to about 4 hours.

20. The method of claim 14, wherein in the step c, the steps a and b are performed once daily for 14 or more days.

21. The method of claim 14, wherein in the step c, the steps a and b are performed twice daily for 14 or more days.

22. The method of claim 14, wherein in the step c, the steps a and b are performed thrice daily for 14 or more days.

23. The method of claim 14, wherein the cooling device has a temperature controller that can be used to adjust the temperature of the part of the cooling device that contacts the human subject.

24. The method of claim 14, wherein the electroacupuncture is applied simultaneously during the cooling period.

25. The method of claim 14, wherein the electroacupuncture is applied prior to the cooling period.

26. The method of claim 14, wherein the electroacupuncture is applied in a period that overlaps the cooling period.

* * * * *